US010435417B2

(12) United States Patent
Platzek et al.

(10) Patent No.: US 10,435,417 B2
(45) Date of Patent: Oct. 8, 2019

(54) PREPARATION OF HIGH-PURITY GADOBUTROL

(71) Applicant: BAYER INTELLECTUAL PROPERTY GMBH, Monheim (DE)

(72) Inventors: Johannes Platzek, Berlin (DE); Wilhelm Trentmann, Munster (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 11 days.

(21) Appl. No.: 15/664,060

(22) Filed: Jul. 31, 2017

(65) Prior Publication Data

US 2018/0105537 A1 Apr. 19, 2018

Related U.S. Application Data

(62) Division of application No. 14/112,994, filed as application No. PCT/EP2012/057013 on Apr. 17, 2012, now Pat. No. 10,072,027.

(30) Foreign Application Priority Data

Apr. 21, 2011 (DE) ........................ 10 2011 100 128

(51) Int. Cl.
C07F 5/00 (2006.01)
A61K 49/10 (2006.01)
C07D 257/02 (2006.01)

(52) U.S. Cl.
CPC ............ C07F 5/003 (2013.01); A61K 49/106 (2013.01); C07D 257/02 (2013.01)

(58) Field of Classification Search
None
See application file for complete search history.

(56) References Cited

U.S. PATENT DOCUMENTS

| | | | |
|---|---|---|---|
| 4,885,363 A | 12/1989 | Tweedle et al. |
| 4,963,344 A | 10/1990 | Gries et al. |
| 5,098,692 A | 3/1992 | Gries et al. |
| 5,277,895 A | 1/1994 | Platzek et al. |
| 5,386,028 A | 1/1995 | Tilstam et al. |
| 5,410,043 A | 4/1995 | Platzek et al. |
| 5,744,616 A | 4/1998 | Petrov et al. |
| 5,871,709 A | 2/1999 | Gries et al. |
| 5,980,864 A | 11/1999 | Platzek et al. |
| 5,994,536 A | 11/1999 | Petrov et al. |
| 6,066,259 A | 5/2000 | Viscardi et al. |
| 6,894,151 B2 | 5/2005 | Platzek et al. |
| 7,385,041 B2 | 6/2008 | Chang et al. |
| 9,447,053 B2 | 9/2016 | Platzek et al. |
| 2013/0116429 A1 | 5/2013 | Platzek |

FOREIGN PATENT DOCUMENTS

| | | |
|---|---|---|
| AT | 397465 B | 4/1994 |
| CA | 1341176 | 1/2001 |
| CA | 2102461 C | 1/2005 |
| CA | 2084582 C | 9/2005 |
| DE | 102010013833 A1 | 9/2011 |
| EP | 0743283 | 11/1996 |
| EP | 0988294 | 11/2005 |
| WO | 9324469 A1 | 12/1993 |
| WO | 98056775 | 12/1998 |
| WO | 2011054480 A1 | 5/2011 |
| WO | 2011151347 A1 | 12/2011 |
| WO | 2016105172 A2 | 6/2016 |

OTHER PUBLICATIONS

Exhibit A (Affidavit of Johannes Platzek submitted on Dec. 1, 2016 in U.S. Appl. No. 14/112,994).*
Exhibit B (Affidavit of Dr. F. Ekkehardt Hahn, submitted on Aug. 31, 2017 in U.S. Appl. No. 14/112,994).*
Platzek, et al., Synthesis and Structure of a New Macrocyclic Polyhydroxylated Gadolinium Chelate Used as a Contrast Agent for Magnetic Resonance Imaging. Inorg. Chem., 1997, pp. 6086-6093, vol. 36 No. 26.
International Preliminary Report on Patentability and Written Opinion dated Oct. 22, 2013 from PCT/EP12/57013.
International Search Report dated Aug. 8, 2012 from PCT/EP12/57013.
Toth, et al., Equilibrium and kinetic studies on complexes of 10-[2,3-dihydroxy-(1-hydroxymethyl)-propl]-1,3,7,10-tetraazacyclododecane-1,4,7-triacetate. Inorganica Chimia Acta 246. (1996) 191-199.
Bourichi, et al. "Solid-state characterization and impurities determination of fluconazol generic products marketed in Morocco". Journal of Pharmaceutical Analysis. 2012. 2(6): 412-421.
Cacheris, et al., "The Relationship Between Thermodynamics and the Toxicity of Gadolinium Complexes". Magnetic Resonance Imaging, vol. 8, No. 4, 1990.
Lovblad, "Gadovist in Multiple Sclerosis", Touch Briefings European Neurological Review, pp. 59-60, 2008.
"Gadovist South African Packaging Insert", 2005.
Tombach; et al., "Comparison of 1.0 M gadobutrol and 0.5 M gadopentate dimeglumine-enhanced MRI in 471 patients with known or suspected renal lesions: results of a multicenter, single-blind, interindividual, randomized clinical phase III trail", Eur. Radiol., 2008, 18, 2610-2619.

* cited by examiner

Primary Examiner — Patricia Duffy
Assistant Examiner — Garen Gotfredson
(74) Attorney, Agent, or Firm — Joseph L. Kent; David Schramm; James R. Stevenson

(57) ABSTRACT

A process for producing high-purity gadobutrol in a purity (according to HPLC) of more than 99.7 or 99.8 or 99.9% and the use for preparing a pharmaceutical formulation for parenteral administration is described. The process is carried out using specifically controlled crystallization conditions.

20 Claims, 12 Drawing Sheets

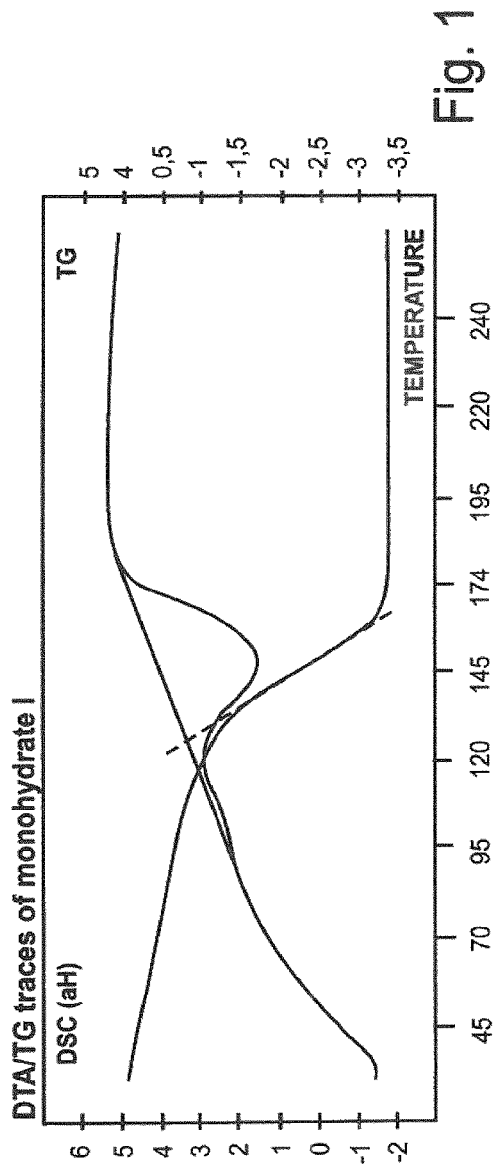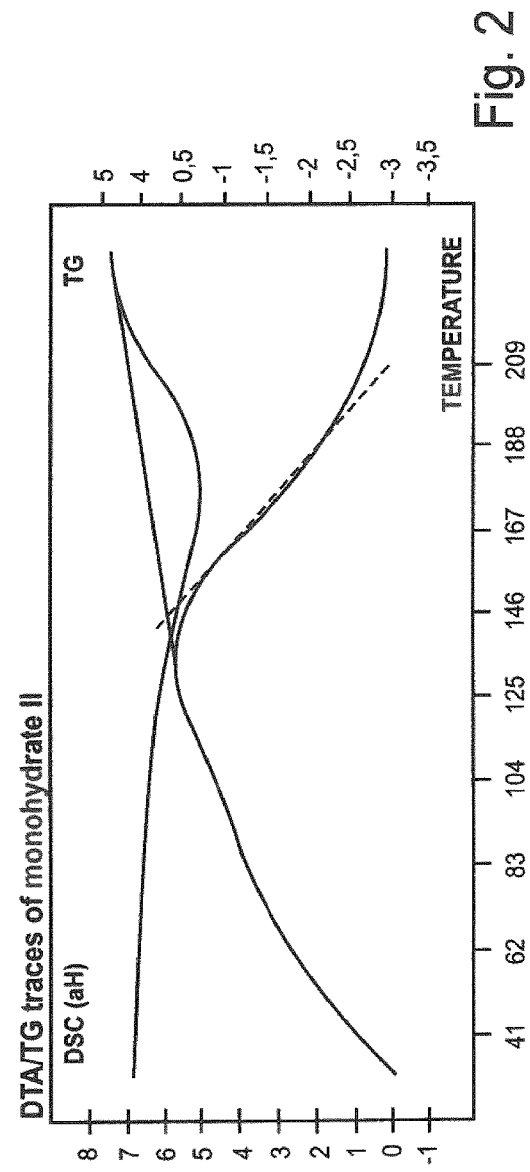

X-ray diffractogram of polymorph I monohydrate I (above) compared to the calculated theoretical diffractogram of the monohydrate (below)

X-ray diffractogram of polymorph II monohydrate II

X-ray diffractogram of amorphous gadobutrol*

IR spectrum of monohydrate I (nujol preparation)

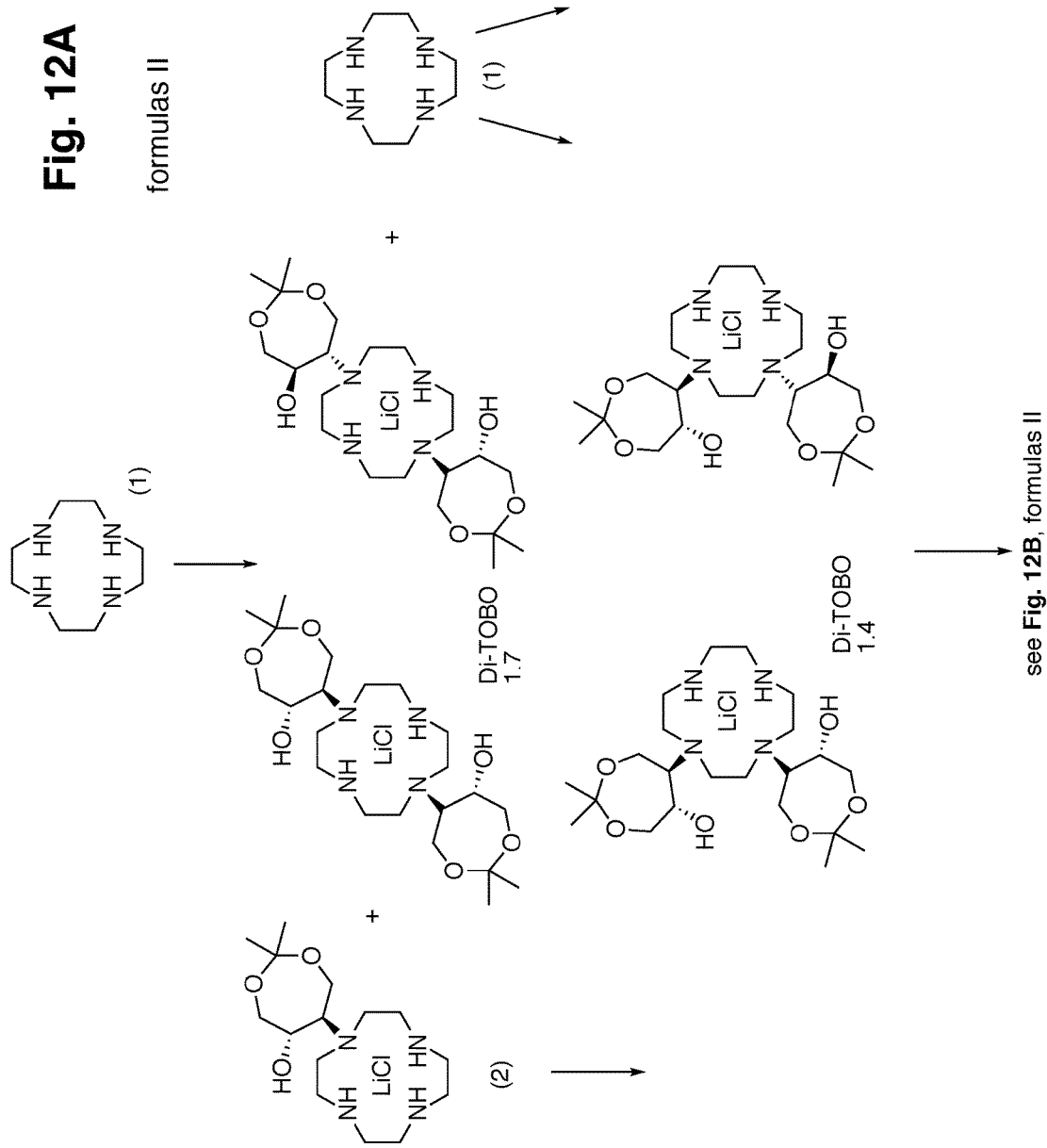
Fig. 12A formulas II

PREPARATION OF HIGH-PURITY GADOBUTROL

CROSS REFERENCE TO RELATED APPLICATIONS

The present application is a divisional of U.S. Ser. No. 14/112,994, filed Jan. 3, 2014, which is a U.S. national phase application under 35 U.S.C. § 371 of International PCT Application PCT/EP2012/057013, filed Apr. 17, 2012, which claims priority to German Patent Application No. 10 2011 100128.3 filed Apr. 21, 2011, the disclosures of each of which are incorporated herein.

FIELD OF DISCLOSURE

The invention relates to a process for preparing high-purity gadobutrol, to gadobutrol in a purity of more than 99.7 or 99.8 or 99.9% and to the use for preparing a pharmaceutical formulation for parenteral application.

BACKGROUND

The more recent developments in the field of the gadolinium-containing MR contrast agents (EP 0448191 B1, U.S. Pat. No. 5,980,864, EP 0643705 B1, EP 0986548 B1, EP 0596586 B1) include the MRI contrast agent gadobutrol (Gadovist® 1.0) which has been approved for a relatively long time in Europe and more recently also in the USA under the name Gadavist® (Bayer HealthCare LLC, Whippany, N.J.).

The contrast action is based on gadobutrol, a non-ionic complex consisting of gadolinium(III) and the macrocyclic ligand dihydroxyhydroxymethyl propyltetraazacyclododecanetriacetic acid (butrol), which leads inter alia at the clinically recommended dosages to shorter relaxation times of protons of the tissue water.

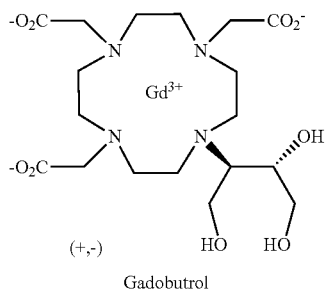

Gadobutrol

Owing to their importance as imaging diagnostics, in particular as MRI diagnostics, metal complexes, in particular the gadolinium complex N-(1-hydroxymethyl-2,3-dihydroxypropyl)-1,4,7-triscarboxymethyl-1,4,7,10-tetraazacyclododecane "gadobutrol" (DE 4009119) can be prepared by various routes. In spite of progress made compared to the original processes, there is still a need for syntheses which are more environmentally friendly and cost-effective, and are suitable for implementation especially on an industrial scale. In particular, there is a high demand for high product throughput and high quality. In more recent years, there has been a trend to replace some or all of the open-chain contrast agents by cyclic contrast agents. Here, there is the requirement to produce particularly pure products, which should additionally also be cost-effective. In general, these are requirements which are mutually exclusive, since high-quality products are expensive to produce owing to specific purification measures. For optimum quality control, it is necessary to have available a highly reliable method for analytical determination which allows detection and quantification of all minor components present.

Accordingly, there is a need for an economically favourable process for producing gadobutrol, and also for an analytical method which allows the selective detection and quantification of minimal amounts of minor components (production monitoring).

BRIEF SUMMARY

Very important aspects in the preparation of gadobutrol are quality and production costs of the end product. Owing to regulatory requirements, high quality standards have to be met. Of interest in this context are purity and content of the active compound. Coupled to purity, it is in particular the spectrum of by-products which needs to be monitored. Minor components have to be toxicologically qualified and assessed. Accordingly, they are listed in specifications and the maximum occurrence in the product is defined. For reasons of product safety and for the good of the patient, the by-product spectrum and/or the presence of individual contaminants are kept as low as possible.

In this context, the polymorphism of the active compound is of importance, since this is closely related to the solubility in water and the shelf-life. Accordingly, it is desirable for the process according to the invention to produce the polymorphous form which has the best solubility in water and is most storage-stable.

The prior art describes the high-yield preparation of gadobutrol starting with cyclen (1,4,7,10-tetraazacyclododecane) of the formula 1, which is known from the literature (DE19608307).

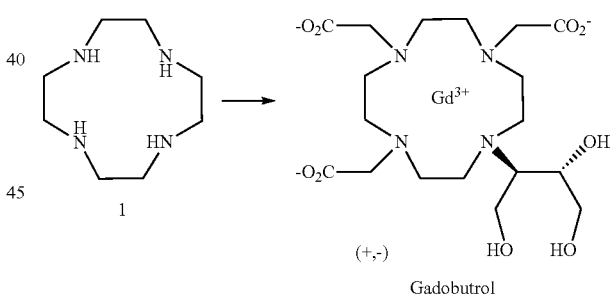

The closest prior art (Inorg. Chem. 1997, 36, 6086-6093 and DE 19724186 A, DE19608307 A) and EP 1343770 B1 describes processes where the butrol ligand is isolated as a lithium complex and converted further into the end product.

BRIEF DESCRIPTION OF THE DRAWINGS

FIG. 1 illustrates DTA/TG traces of Gadobutrol monohydrate I.

FIG. 2 illustrates DTA/TG traces of Gadobutrol monohydrate II.

FIGS. 12A and 12B illustrate formulas for a synthesis according to one aspect.

DETAILED DESCRIPTION

Figure 3:
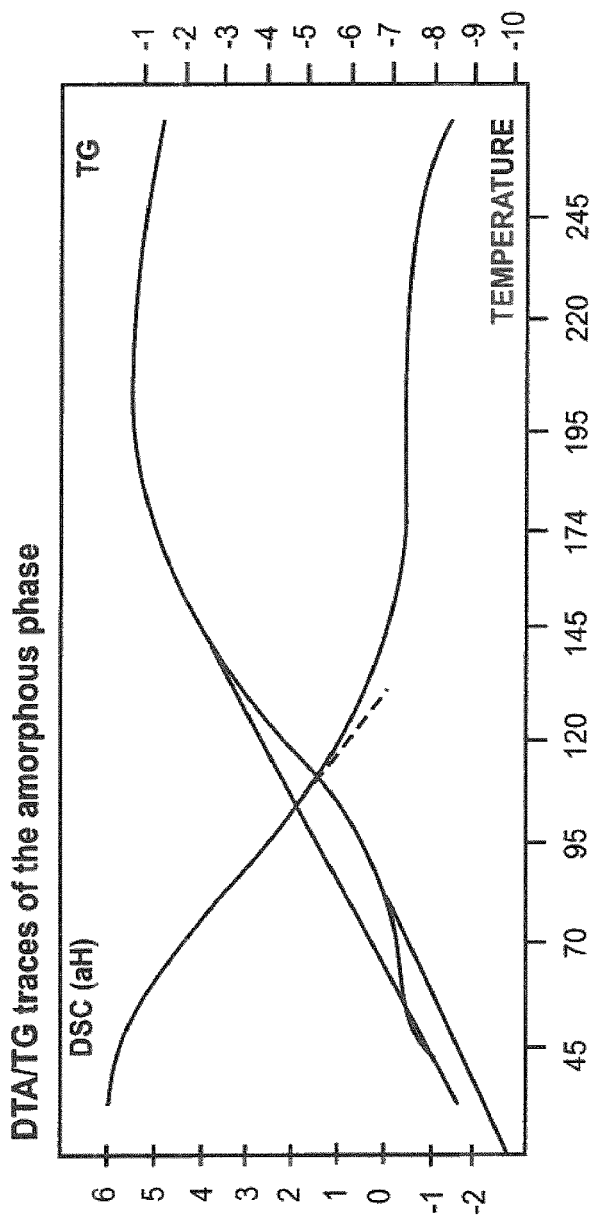
FIG. 3 illustrates DTA/TG traces of Gadobutrol amorphous Phase.

It is an object of the present invention to provide a process which allows gadobutrol to be produced in high yield and in the highest purity (conforming to the specification).

This object is achieved by the invention, a process for producing high-purity gadobutrol (=the gadolinium complex of N-(1-hydroxymethyl-2,3-dihydroxypropyl)-1,4,7-triscarboxymethyl-1,4,7,10-tetraazacyclododecane) which comprises the reaction of the starting material cyclen (1,4,7,10-tetraazacyclododecane) with 4,4-dimethyl-3,5,8-trioxabicyclo[5,1,0]octane and lithium chloride in alcohol at elevated temperatures, alkylation with sodium monochloroacetate in alkaline medium, work-up under acidic conditions, removal of the salts and addition of gadolinium oxide, then the adjustment of the pH with lithium hydroxide to a neutral to slightly basic value, concentration of the solution and addition of alcohol, then heating under reflux and, after cooling, isolation and drying of the crude product, dissolution of the crude product in water and purification on an ion exchanger, then treatment with activated carbon followed by sterile filtration, then boiling under reflux, cooling and isolation and drying of the product.

This is in particular a process where the starting material cyclen (1,4,7,10-tetraazacyclododecane) is reacted with 4,4-dimethyl-3,5,8-trioxabicyclo[5,1,0]octane and lithium chloride in isopropanol at elevated temperatures, then distilled on water and alkylated with sodium monochloroacetate in alkaline medium, worked up under hydrochloric conditions, the salts are removed by addition of methanol and the crude ligand is reacted with gadolinium oxide in water at elevated temperatures, the pH is then adjusted with lithium hydroxide to 7.1-7.4, the solution is concentrated and ethanol is added in such an amount that a water content of 7-9.5%, preferably 8.0-9.0%, is reached, the mixture is then heated under reflux for at least 60 minutes and the crude product is, after cooling, isolated and dried, preferably dried at 46°-48° C., the crude product is then dissolved in water and purified on an ion exchanger cascade, where the solution is passed first through the acidic and then through the basic ion exchanger, the purified solution, which has a conductance of <40 µS/cm, is then concentrated, treated with activated carbon, subjected to sterile filtration and, by metered addition of ethanol, adjusted to a water content in the range 10-12%, preferably of about 11%, then boiled under reflux and cooled, and the product is isolated and dried.

This is in particular a process where the starting material cyclen (1,4,7,10-tetraazacyclododecane) is reacted with 4,4-dimethyl-3,5,8-trioxabicyclo[5,1,0]octane and lithium chloride in isopropanol at elevated temperatures, then distilled on water and alkylated with sodium monochloroacetate in alkaline medium and worked up under hydrochloric conditions, the salts are removed by addition of methanol and the crude ligand is reacted with gadolinium oxide in water at elevated temperatures, the pH is then adjusted with lithium hydroxide to 7.1-7.4, the solution is concentrated and ethanol is added in such an amount that a water content of particularly preferably 8.5% is reached, the mixture is then heated under reflux for at least 60 minutes and the crude product is, after cooling, isolated and dried at 46°-48° C., the crude product is then dissolved in water and purified on an ion exchanger cascade, where the solution is passed first through the acidic and then through the basic ion exchanger, the purified solution, which has a conductance of <20 µS/cm, is then concentrated, treated with activated carbon, then subjected to sterile filtration and, by metered addition of ethanol over a period of 120 minutes, adjusted to a water content of 10-12%, preferably 11%, then boiled under reflux and cooled, and the product is isolated and dried, preferably dried at 53-55° C.

For the ion exchanger cascades, the following exchangers are employed in the process: Suitable exchangers are the customary commercial ion exchangers. Advantageously, the acidic ion exchanger used is Amberlite IRC 50, and the basic exchanger used is IRA 67. After this purification by an ion exchanger cascade, where the solution is passed first through the acidic and then through the basic ion exchanger, the thus purified solution, which has a conductance of <20 µS/cm, is then concentrated, treated with activated carbon, such as Norit SX Plus activated carbon, then subjected to sterile filtration and, by metered addition of ethanol over a period of 120 minutes, adjusted to a water content of preferably 11%, then boiled under reflux and cooled, and the product is isolated and dried at 53-55° C.

A detailed description of the novel process according to the invention is given in detail:

After complexation of the butrol ligand, present in aqueous solution, with gadolinium oxide (120 minutes, 90° C.) and adjustment of the pH with lithium hydroxide monohydrate to pH 7.1-7.4, the mixture is substantially concentrated under reduced pressure. Ethanol is added to the solution that remains. Here, it is ensured that the final water content reached is 7.0-9.5%, preferably 8.0-9.0%, and particularly preferably 8.5% (this is achieved by further addition of ethanol or alternatively water). The mixture is heated under reflux (60 minutes), and stirring is continued at a jacket temperature of 100° C. for 480 minutes. The mixture is cooled to 20° C. The crude product is isolated using a centrifuge or pressure nutsch, and the filter cake is washed with ethanol and then dried at 58° C. (jacket) under reduced pressure until an internal temperature of 48° C. is reached.

Figure 14:
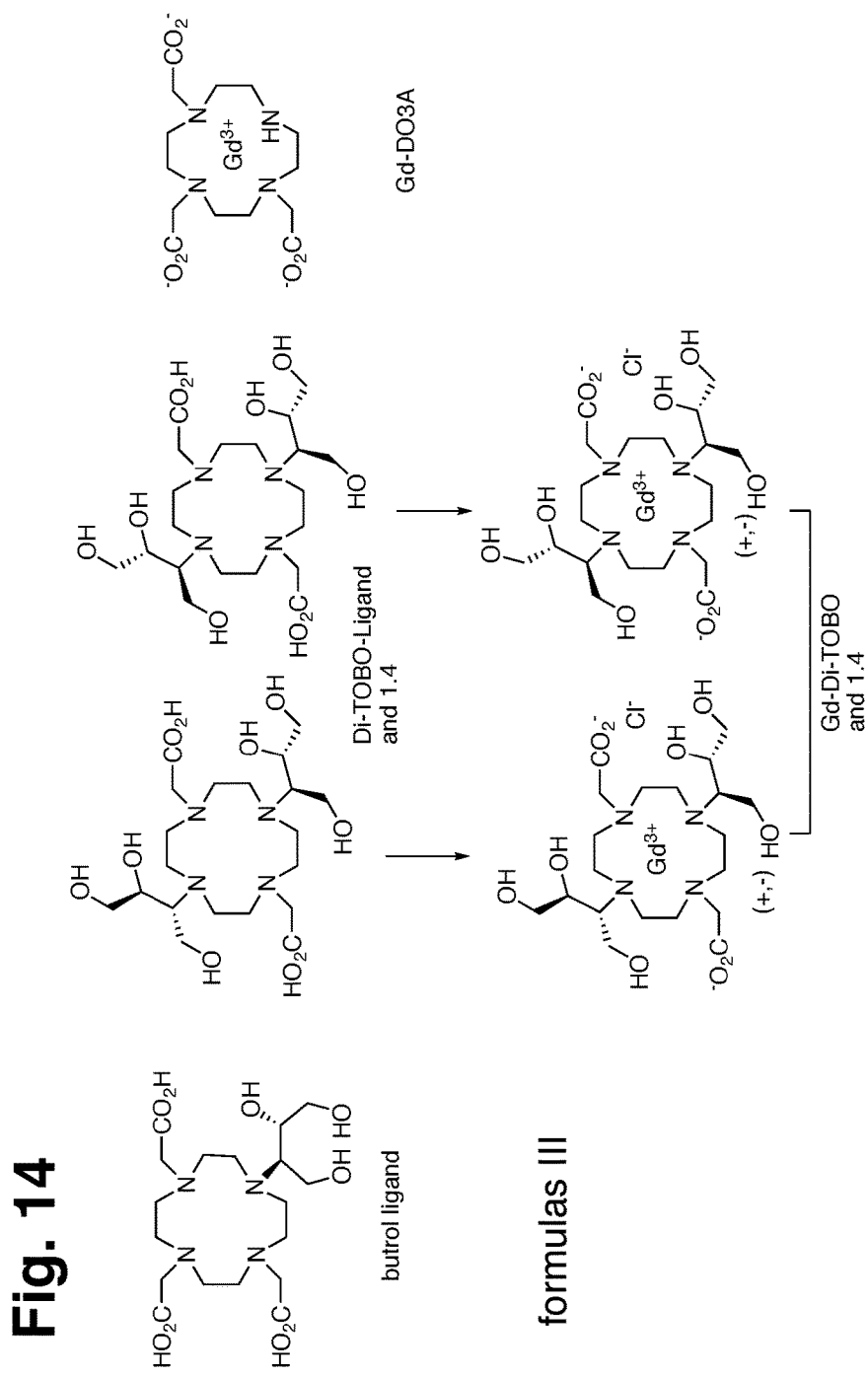
FIG. 14 illustrates formulas for a synthesis according to one aspect.

The crude product (gadobutrol, crude) is dissolved in water. Further purification is effected via an ion exchanger cascade in the manner below: the aqueous solution is initially added to an acidic ion exchanger AMBERLITE IRC 50. The eluate is then added directly to the basic exchanger IRA 67. The eluate is pumped back onto the acidic exchanger etc. The solution is recycled until the conductivity of the solution has reached a value of <20 uS/cm. On a thin-layer evaporator, the solution is then concentrated carefully and gently at 50 mbar. The ion exchanger treatment affords a product which is already of very high quality. Analysis shows that very small amounts of the following components are still present: See FIG. 14, formula III Owing to its negative charge, Gd-DOTA is adsorbed completely on the anion exchanger. Gd-DO3A is an electrically neutral compound and is therefore not absorbed on the ion exchanger. In contrast to the other two impurities (di-TOBO ligands and butrol ligand), Gd-DO3A has a more lipophilic nature. However, surprisingly, analysis detects the diastereomeric di-TOBO ligands (the potential Gd complexes, which are not very stable, may lose gadolinium on the cation exchanger). Moreover, the occurrence of free butrol ligand is observed (here, too, the acidic ion exchanger may remove Gd from the complex). For the person skilled in the art, the occurrence of the di-TOBO ligands and the butrol ligand after this purification step is surprising, since it would be expected that potentially substances containing amine and acid groups would be absorbed quantitatively on the ion exchanger.

Since the 3 by-products mentioned are the critical impurities which in all cases are to be kept as low as possible, a further purification step is required. Here, the conditions have to be chosen such that maximum yield with optimum quality is achieved.

By addition of water, the concentrated product-containing fraction from the ion exchange purification is adjusted to a concentration of from 19.1 to 20.9% (w/w). This is followed by treatment with activated carbon, the purpose of which is the greatest possible reduction of the endotoxin value of the product (preparation for parenteral administration). To this end, the product is stirred with NORIT SX Plus (conductivity 20 µS) at 20° C. for 60 minutes and the n separated from the carbon by filtration, and the filtrate is filtered through a sterile filtration candle and concentrated gently under reduced pressure (jacket temperature at most 80° C.). The jacket temperature is lowered to 75° C. and a first partial amount of ethanol is added, a second partial amount of ethanol is then added over a period of 120 minutes such that the (internal) temperature does not drop below 72° C. The water content of the solution is determined according to Karl-Fischer. The value should be from 10.0 to 12.0, preferably 10.5-11.5%, particularly preferably 11%. If the target value is not reached, it may be set accurately by further addition of water or ethanol. The mixture is then boiled under reflux for 120 minutes. The mixture is allowed to cool to 20° C. and the product is isolated using a centrifuge or a pressure nutsch, the filter cake being washed with ethanol.

Drying of gadobutrol, pure, is carried out under reduced pressure at an internal temperature of >53° C. and a jacket temperature of 55° C. The end product is filled into PE pouches coated with aluminium. By appropriate selection of the drying parameters, it is possible to reduce the residual amount of ethanol to <202 ppm.

The invention also relates to gadobutrol of a purity (according to HPLC) of more than 99.7 or 99.8 or 99.9% and to gadobutrol of a purity of more than 99.7 or 99.8 or 99.9%, comprising free gadolinium(III) ions in an amount of less than 0.01%, having a residual ethanol solvent content of less than 200 ppm and comprising the butrol ligand (=N-(1-hydroxymethyl-2,3-dihydroxypropyl)-1,4,7-triscarboxymethyl-1,4,7,10-tetraazacyclododecane) in a proportion of less than 0.03%.

One requirement is to keep the content of free complex former (butrol ligand, formula 3) as low as possible.

During the preparation of the pharmaceutical GADOVIST® a slight excess of complex former (of the order of about 0.1%) in the form of the calcium/butrol complex ("Calcobutrol", *Inorg. Chem.* 1997, 36, 6086-6093) is added to the formulation. Calcobutrol is an additive in the pharmaceutical formulations of gadobutrol and has the task of preventing a release of free gadolinium in the formulation (solutions) (see EP 0 270 483 B2).

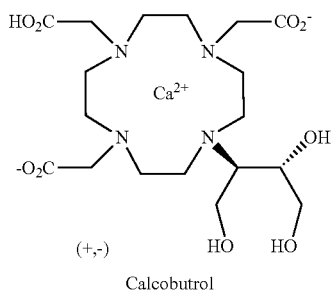

Calcobutrol

This approach ensures maximum stability of the aqueous solutions and allows storage over a relatively long period of time. The problem encountered during storage of gadolinium-comprising contrast agents in aqueous solution is the trans-chelation of gadolinium from the complex with metal ions from the glass of the vials (for example Zn, Cr, etc.), which also form stable complexes and would result in the formation of toxic free gadolinium ions. If no excess of complex former is added to the formulation, free gadolinium is formed. In contrast, the thermodynamically less stable calcium complex of the butrol ligand readily exchanges the calcium. Since calcium is an element which occurs naturally in the body, it is toxicologically acceptable and thus ensures absolute patient safety (the formation of free gadolinium can be excluded with absolute certainty).

The excess of complex former (in form of the calcium complex) in the formulation is limited by a very narrow specification (0.08-0.14%), and the use of high-purity gadobutrol in which the proportion of butrol ligand is as low as possible is therefore a pre-condition since otherwise the total complex former excess would be >0.14 mol % (sum of calcium/butrol complex and butrol ligand). This leads to "out of spec" batches, i.e. batches that do not meet the specification, in the pharmaceutical production, which would result in considerable economical losses. This represented a serious problem in the initial preparation of gadobutrol, and there was therefore a pressing need to control this minor component (butrol ligand) by a stable production process and by a sensitive analytical method.

An essential pre-condition for the preparation of high-purity gadobutrol is a special analytical method which allows detection and quantification of main products and by-products (impurities). For a long time, the main problem specifically in gadobutrol analysis was this quantification of the proportion of free butrol ligand. Since detection was only by a non-selective titration method (see examples), the di-TOBO ligands (see formula scheme below) were also measured and the sum was displayed. All gadobutrol batches prepared in accordance with the prior art were characterized by this "sum method". With regard to the above-described critical limit based on the content of free complex former (butrol ligand), this was an absolutely unsatisfactory situation, which needed to be resolved. In addition to the object of providing an optimum preparation process affording a product of excellent quality, it was therefore another object to provide an analytical process for selective monitoring of the main impurities allowing the determination of the content of butrol ligand and di-TOBO ligand with an accuracy of <0.01%. Only by combining analysis and preparation process, it is possible to produce gadobutrol of >99.7% (=>99.9% one spot/peak quality).

The novel process according to the invention makes it possible, by combination of specifically controlled crystallization conditions, along with a highly selective analytical method, to detect byproducts<0.01%, and thus to provide very good control over the purity of the active compound gadobutrol, and to keep the impurity level as low as possible.

Figure 12B:
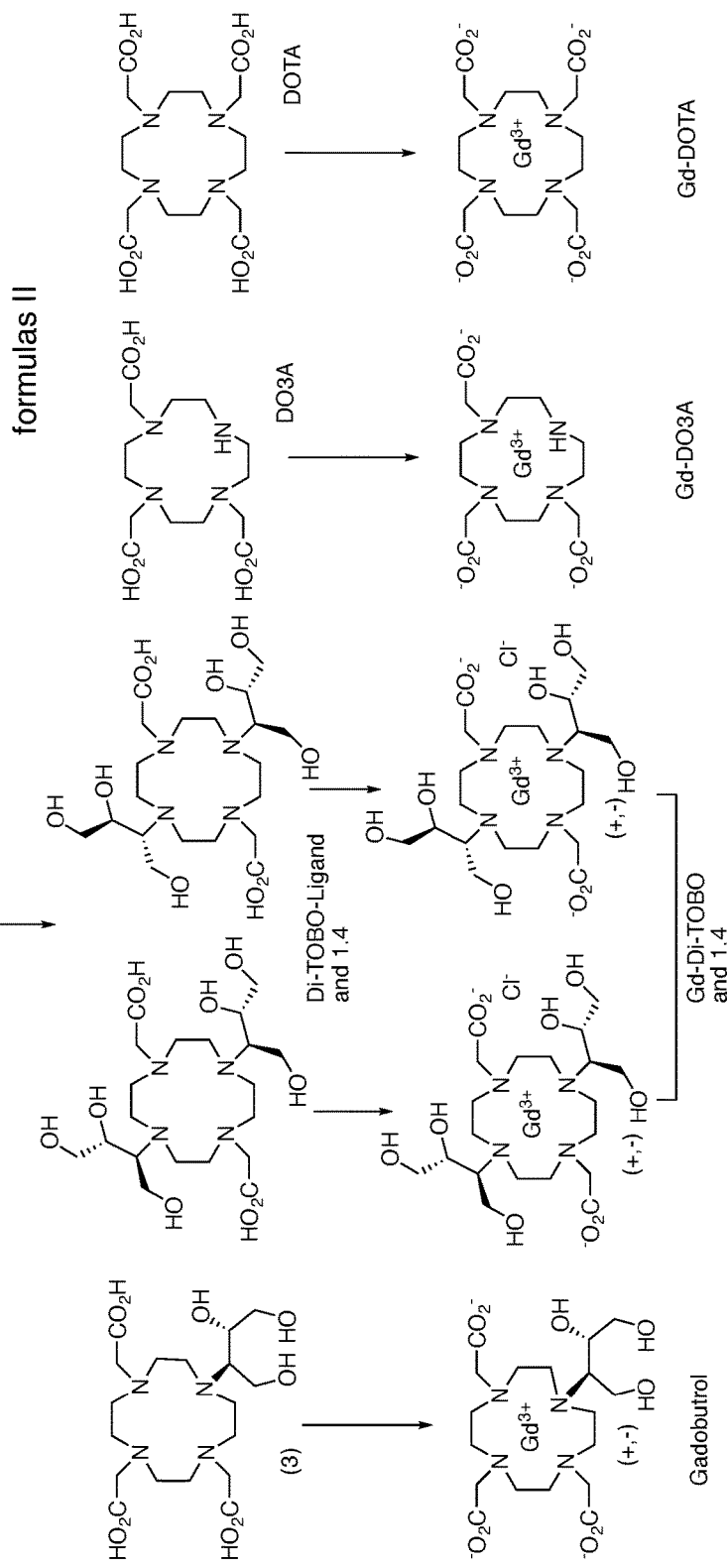

The preparation scheme, see FIG. 12, serves to illustrate the origin of the main impurities of gadobutrol: See FIG. 12, formulas II Starting with cyclen (1,4,7,10-tetraazacyclododecane), which is known from the literature, in a first step the bicyclotrioxaoctane ring (TOBO) is fused on as described in EP 0986548 B1 (Schering AG) (opening of the epoxide with lithium chloride in isopropanol under reflux leads to the N-(6-hydroxy-2,2-dimethyl-1,3-dioxepan-5-yl)-1,4,7,10-tetraazacyclododecane/LiCl complex). In addition to the desired mono-substituted compound, two further compounds are obtained as by-products. These are the doubly alkylated products (Di-TOBO=1,7- and 1,4-bis(N-(6-hydroxy-2,2-dimethyl-1,3-dioxepan-5-yl)-1,4,7,10-tetraazacyclododecan/LiCl complex), which are likewise obtained in the form of the Li complexes (4 diastereomers of 1,4- and 1,7-substituted compounds in racemic form, i.e. a total of 8 species). After the reaction, the products are not isolated but the mixture is directly processed further. The crude product of this reaction step still comprises residual unreacted cyclen (1) which is carried over into the next step (by distillation, the isopropanol solvent is replaced with water).

In the next step, using the sodium salt of chloroacetic acid, the products are alkylated under basic-controlled conditions to give the corresponding acetic acids (butrol stage). It is important to keep the pH>12 at all times. In this process step, the impurities contained in the main product are alkylated, too, giving a characteristic impurity spectrum at this stage. In addition to the diastereomeric DI-TOBO ligands, DOTA and DO3A (by incomplete alkylation) are formed from the cyclen. Following acidic work-up with hydrochloric acid, the salts (mainly NaCl) are filtered off after addition of methanol and the butrol ligand is prepared as an aqueous solution for complexation with gadolinium oxide.

Complexation with gadolinium oxide in water gives a corresponding crude product which, as main component, comprises essentially gadobutrol. However, the by-products described above are likewise gadolinium-complexing ligands, and they afford the corresponding Gd complexes (4 diastereomeric Gd-di-TOBO complexes, Gd-DOTA, Gd-DO3A).

In these respects, the process is analogous to the prior art procedure. The prior art describes the use of ethanol for crystallization of crude and pure gadobutrol, and aqueous ethanol is also mentioned.

Surprisingly, it has now been found that, by appropriate selection of the crystallization parameters both at the gadobutrol crude and pure stages, it is possible to achieve excellent yields and superior product qualities.

What is novel is the specific procedure described below which allows the preparation of high-purity gadobutrol having purities (according to HPLC) of >99.7 or 99.8 or 99.9% in 4 process steps:

| Process step | Process | Critical limits |
|---|---|---|
| 1. | Crystallization from ethanol having a defined water content affords a crude product: gadobutrol, crude | Water content 7.0-9.5% preferably 8.0-9.0% particularly preferably 8.5% |
| 2. | Ion exchanger purification gives an aqueous solution of gadobutrol which is already highly purified | Conductivity <20 uS/cm it is important that the solution is passed through the acidic exchanger first. |
| 3. | Crystallization from ethanol having a defined water content affords a crude product: gadobutrol, pure | Water content 10-12% preferably 10.5-11.5% particularly preferably 11% |
| 4. | Drying under reduced pressure | >53° C. and <55° C. |

An important factor in the novel process according to the invention is, surprisingly, the exact adjustment to a particular water content in the crystallization of both the crude and the pure product. Surprisingly, the limits are very narrow and yield optimum results only in this range. Surprisingly, by selecting a specific water content, it is possible to decrease the amount of both lipophilic impurities (for example DO3A) and also strongly hydrophilic impurities (Di-TOBO ligands, butrol ligand), with an optimum total yield of gadobutrol. For the person skilled in the art, this was not obvious, and it was therefore surprising for all.

The total yields obtained in the novel process according to the invention (starting with cyclen) are excellent and are shown in the table below:

| Process step | Yield |
|---|---|
| Cyclen to gadobutrol, crude | almost quantitative (>96%) |
| Ion exchanger purification | 74.1% |
| Final crystallization | 96.9% |
| Total yield (starting from cyclen) | 70% |

Figure 4:
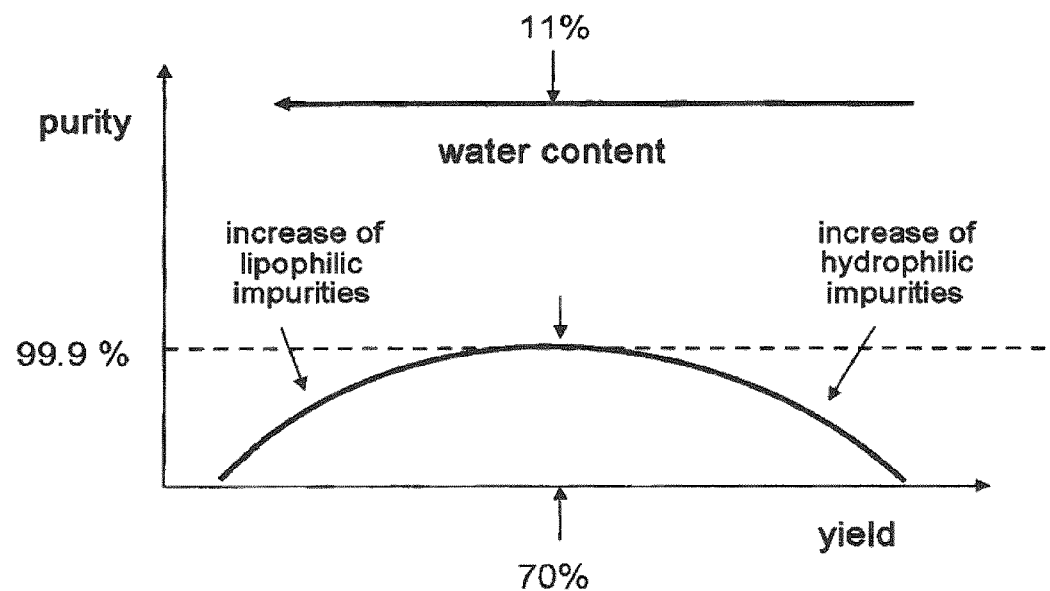
FIG. 4 shows yield, purity and water contents of Gadobutrol after final crystallization.

In combination with the very high purity, such a high total yield leads to a significant improvement in economic terms of the production process. The schematic representation in FIG. 4 summarizes how total yield and purity are related to water content in the final crystallization (the principle also applies to the first crystallization): See FIG. 4 Yield, purity and water contents after final crystallisation.

With increasing water content (left side), a decrease in yield and at the same time an increase of lipophilic impurities is observed. With decreasing water content (right side), the yield increases; however, at the same time the proportion of hydrophilic impurities increases. Accordingly, it was very surprising that such a high total yield (compared to the prior art) can be achieved combined with excellent quality.

A further important point of the process according to the invention is based on the fact that virtually only one main polymorph is obtained in the preparation (a second unwanted polymorph is also observed, but only in insignificant amounts). The physical properties are of high interest and very important because they are related to storage stability and solubility of the product. With a long shelf-life, it is possible to manufacture stocks of product which can then be used to produce the pharmaceutical preparation, in the present case GADOVIST®, on demand. This allows optimum flexibility in the preparation process.

It is found that 2 polymorphs are present in the form of the monohydrates (water content 3-3.5%): Monohydrate I and monohydrate II (see examples in the later part)

It has been found that, when a very high purity, preferably >99.7 or >99.8 or >99.9%, is reached, what is present is substantially polymorph I. This is important since this polymorph also has more favourable properties compared to polymorph II, in particular with regard to the solubility of the polymorphs in water. The better solubility of polymorph I ensures optimum preparation of the pharmaceutical formulations (solutions for parenteral administration in water). Of particular interest here is the 1 molar GADOVIST® solution which is based specifically on the high solubility of gadobutrol. The better the solubility of the material in the pharmaceutical production, the better and the more reproducible the process. This ensures high safety and reproducibility in the preparation.

Solubility of Polymorphs I and II in Water

The table below shows the solubility of the two polymorphs I and II of gadobutrol at 20° C. in water

| Polymorph | Solubility in water (g/l) |
|---|---|
| Monohydrate I | 1081 ± 2 |
| Monohydrate II | 922 ± 9 |

The values determined for the solubility of gadobutrol show that it is soluble in water in almost any ratio. Surprisingly, polymorph I monohydrate I is more soluble than monohydrate II. This is favourable with respect to the preparation process of the formulation, but has no effect on the safety of the preparation (in the case of polymorph II, longer stirring is required/in general, batches comprising a proportion of polymorph II are not used for the sake of a standardized preparation process).

Stability on Storage

Three batches of monohydrate I and one batch of monohydrate II were stored under ICH conditions. Both forms remained unchanged for 6 months at 40° C./75% relative atmospheric humidity and for 36 months at 25° C./60% relative atmospheric humidity and 30° C./75% relative atmospheric humidity. No decomposition products were observed, and no other parameters of the specification were changed substantially. On storage, the batches maintained their solid state.

Behaviour of the Monohydrates During the Preparation of the Pharmaceutical

Differences between the two monohydrates I and II were observed during dissolution of the active compound. In general, the time required to get monohydrate I into solution is 45 minutes at 40-50° C. During this time, monohydrate II was incompletely dissolved. For dissolution, significantly longer periods of time were required.

Analytical Characterization of Gadobutrol

As already mentioned, the main problem in the analysis was the analysis of the differentiation and quantification of butrol ligand and di-TOBO ligand. Surprisingly, conditions were found which allow the determination of these main impurities with an analytical accuracy of <0.01%, which represents a major breakthrough in the entire production chain. With this process, for the first time, it was possible to differentiate the crystallization processes with respect to their efficiency and productivity. The tables below show the essential parameters of this method (see also the examples).

| HPLC conditions | |
|---|---|
| Column length: | 250 mm |
| Internal diameter: | 4.6 mm |
| Stationary phase1: | Luna Phenyl-Hexyl 3 μm |
| Column temperature: | 50° C. |
| Autosampler temperature: | 10° C. |
| Flow rate: | 1.0 ml/min |
| Corona detector: | 100 pA |
| UV detector: | 195 nm |
| Flow rate: | 1.0 ml/min |
| Gradient parameters: | |
| Mobile phase A: | 0.0025% strength formic acid + 0.5% acetonitrile |
| Mobile phase B: | acetonitrile |

| Step | Time [min] | A [%] | B [%] | Gradient profile |
|---|---|---|---|---|
| 1 | 0.0 | 100 | 0 | — |
| 2 | 15.0 | 100 | 0 | isocratic |
| 3 | 30.0 | 75 | 25 | linear |
| 4 | 30.1 | 100 | 0 | linear |
| 5 | 40.0 | 100 | 0 | equilibration |

The quality of the gadobutrol batches prepared by the novel process according to the invention for the specific crystallization can be summarized as follows:

| Analytical parameter | Measurement values found |
|---|---|
| Purity (HPLC) | >99.7 or 99.8 or 99.9% |
| Free $Gd^{3+}$ | <0.01% |
| Butrol ligand | <0.03% |
| Di-TOBO ligand | <0.03% |
| Gd-DO3A | <0.03% |
| Unspecified impurities | <0.03% |
| Content | 98-102% |
| Endotoxins | <0.5 EU |
| Residual amount of ethanol solvent | <200 ppm |

The process according to the invention allows the cost-efficient production of gadobutrol in individual batches on a 100 kg scale. Here, by selecting the crystallization parameters, it was possible to achieve optimum yield combined with optimum purity. Owing to the high purity, it is possible to produce polymorph I in a reproducible manner, which means firstly great flexibility with respect to the storage of the active compound and secondly a good dissolution rate in the pharmaceutical production of the formulation.

The invention further comprises the use of the high-purity gadobutrol for producing a pharmaceutical formulation for parenteral administration. The conditions of such a preparation are known from the prior art and are familiar to the person skilled in the art (EP 0448191 B1, CA Patent 1341176, EP 0643705 B1, EP 0986548 B1, EP 0596586 B1).

The invention is illustrated by the examples below, where the following analytical methods were used:

Methods:

1.) Methods Used for Determining the Purity:

The method described below was used first and also served to determine the purities of the preparation processes described in the prior art.

1.1. Method: Non-Selective Photometric Titration of Free Complex Formers

Principle of the Method

The active compound is quantified by titration. The colour change is monitored photometrically.

Reagents
   Sodium hydroxide solution 1N
   Hydrochloric acid 1% [m/V]
   Water
   Rg 0688, indicator/buffer solution III
   Gadolinium sulphate solution 0.00025N standard solution
   Sodium edetate solution 0.00025M standard solution Test Procedure For laboratories comprising robots for automated analysis, the work procedure below does not apply; it is replaced by the corresponding laboratory work procedure.

Test Solution

In a 50 ml beaker, 0.2250-0.2750 g of test substance, m, is dissolved in a 50 ml beaker in 5.00 ml of gadolinium sulphate solution, V[1]. The solution is then heated in a boiling water bath for 15 min. After cooling, 10.0 ml of Rg 0688 indicator/buffer solution III are added, and the pH is adjusted to 5.0 0.1 using 1% hydrochloric acid [w/v] or 1N sodium hydroxide solution. The pH is measured potentiometrically using a combination glass electrode.

Practice

With magnetic stirring, sodium edetate solution, V[2], is titrated into the test solution until the electronically determined end point is reached. The change of colour from violet-red via yellow-orange to yellow is monitored photometrically. Evaluation is carried out by plotting the curve or using the instrument software. The equivalence point is determined by extending the start line and the turning tangent; the titration volume read off corresponds to the standard solution, V[2], consumed.

Test Conditions

Instrument: e.g. Titroprocessor 682, from Metrohm
Photometer: e.g. fibre-optic photometer 662
Wavelength: 570 nm
Transmission starting value: 15%
Burette: e.g. Dosimat 665; metering accuracy 10 ml 0.005 ml
Titration rate: high
Stirrer: intensive stirring Calculation free complex former in %, calc. as butrol (ZK00150307), $$\text{calc. for anhydrous and solvent-free substance} = \frac{(V[1] \times T[1] - V[2] \times T[2]) \times 0.00025 \times 450.49 \times 10}{m \times (100 - (W + LM))}$$

$V[1]$ = consumption of gadolinium sulphate solution in ml $V[2]$ = consumption of sodium edetate standard solution in ml $T[1]$ = titre of gadolinium sulphate solution $T[2]$ = titre of sodium edetate solution $m$ = test substance weighed out, in g $W$ = measurement result of test method water in %

$LM$ = measurement result of test method ethanol in %

450.49 = molar mass of ZK00150307 in g/mol 1 ml of sodium edetate standard solution corresponds to 450.49 mg of ZK00150307.

2.) Novel Selective Method for the Determination of Butrol and Di-TOBO Ligand

In the context of the development of the novel preparation process according to the invention for gadobutrol, a very specific HPLC method for differentiation of butrol ligand from other impurities (e.g.: di-TOBO ligand) was developed:

| Method parameters | |
|---|---|
| HPLC conditions | |
| Column length: | 250 mm |
| Internal diameter: | 4.6 mm |
| Stationary phase1: | Luna Phenyl-Hexyl 3 μm |
| Column temperature: | 50° C. |
| Autosampler temperature: | 10° C. |
| Flow rate: | 1.0 ml/min |
| Corona detector: | 100 pA |
| UV detector: | 195 nm |
| Flow rate: | 1.0 ml/min |
| Gradient parameters: | |
| Mobile phase A: | 0.0025% strength formic acid + 0.5% acetonitrile |
| Mobile phase B: | Acetonitrile |

| Step | Time [min] | A [%] | B [%] | Gradient profile |
|---|---|---|---|---|
| 1 | 0.0 | 100 | 0 | — |
| 2 | 15.0 | 100 | 0 | isocratic |
| 3 | 30.0 | 75 | 25 | linear |
| 4 | 30.1 | 100 | 0 | linear |
| 5 | 40.0 | 100 | 0 | equilibration |

| | |
|---|---|
| Mobile Phase A: | 50 μl of 50% strength formic acid in 995 g of water + 5 ml of ACN pipetted in using a transfer pipette formic acid quality: for HPLC or LC-MS acetonitrile quality: Hypergrade |
| Test solution: | in 10 ml flasks, the samples are dissolved in mobile phase A, and the flask filled to the mark. |
| Injection volume: | 20 μl |
| Notes: | weighed out: 25.0 mg/10 ml The samples have to be filled into polypropylene vials. |

The table below shows the retention times of gadobutrol and the relevant main impurities:

Retention times (RT) and relative retention times (RRT)

| No. | Name | RT [min] | RRT |
|---|---|---|---|
| 1 | di-TOBO ligand | 2.9 | 0.22 |
| 1b | Gd-di-TOBO | 3.3 | 0.25 |
| 2 | Butrol ligand | 4.85 | 0.36 |
| 3 | Gadobutrol | 13.3 | 1.00 |
| 4 | Gd-DO3A | 15.3 | 1.15 |
| 5 | Gd-DOTA | 30.2 | 2.27 |

Synthesis of Gd-Di-TOBO (No. 1b, the Counterion Used was Acetate Instead of Chloride):

For an unambiguous determination method for the gadolinium complex of the di-TOBO ligand, this was specially prepared (EP 0985548 B1, Example 1). However, it was found in the investigations that there is no Gd complex of the di-TOBO ligand present in the end product (the complex is not sufficiently stable and probably decomposes on the acidic ion exchanger).

Figure 5A:
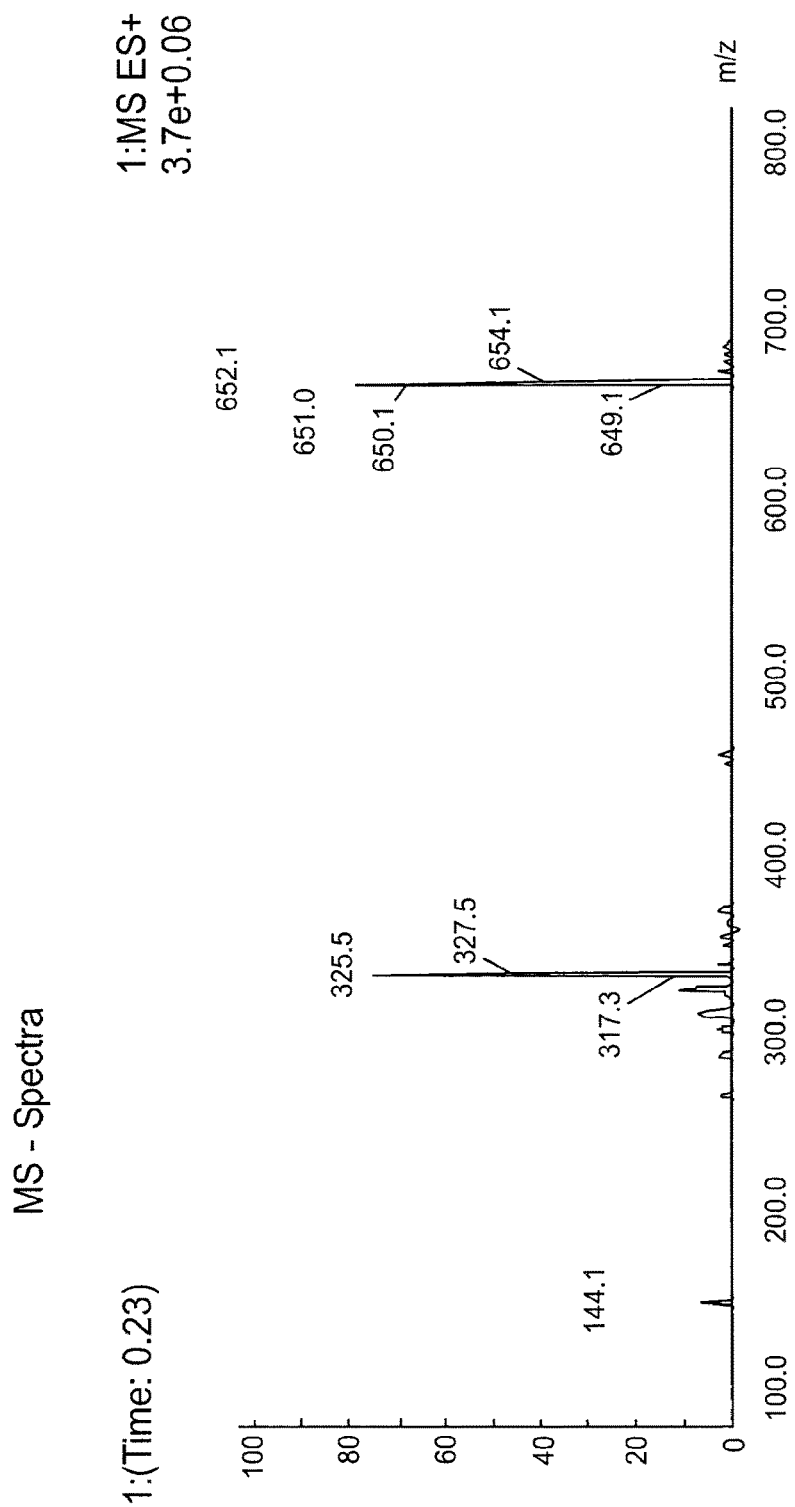
FIGS. 5A and 5B illustrate MS-Spectra of Gadobutrol produced according to one aspect.
Figure 5B:
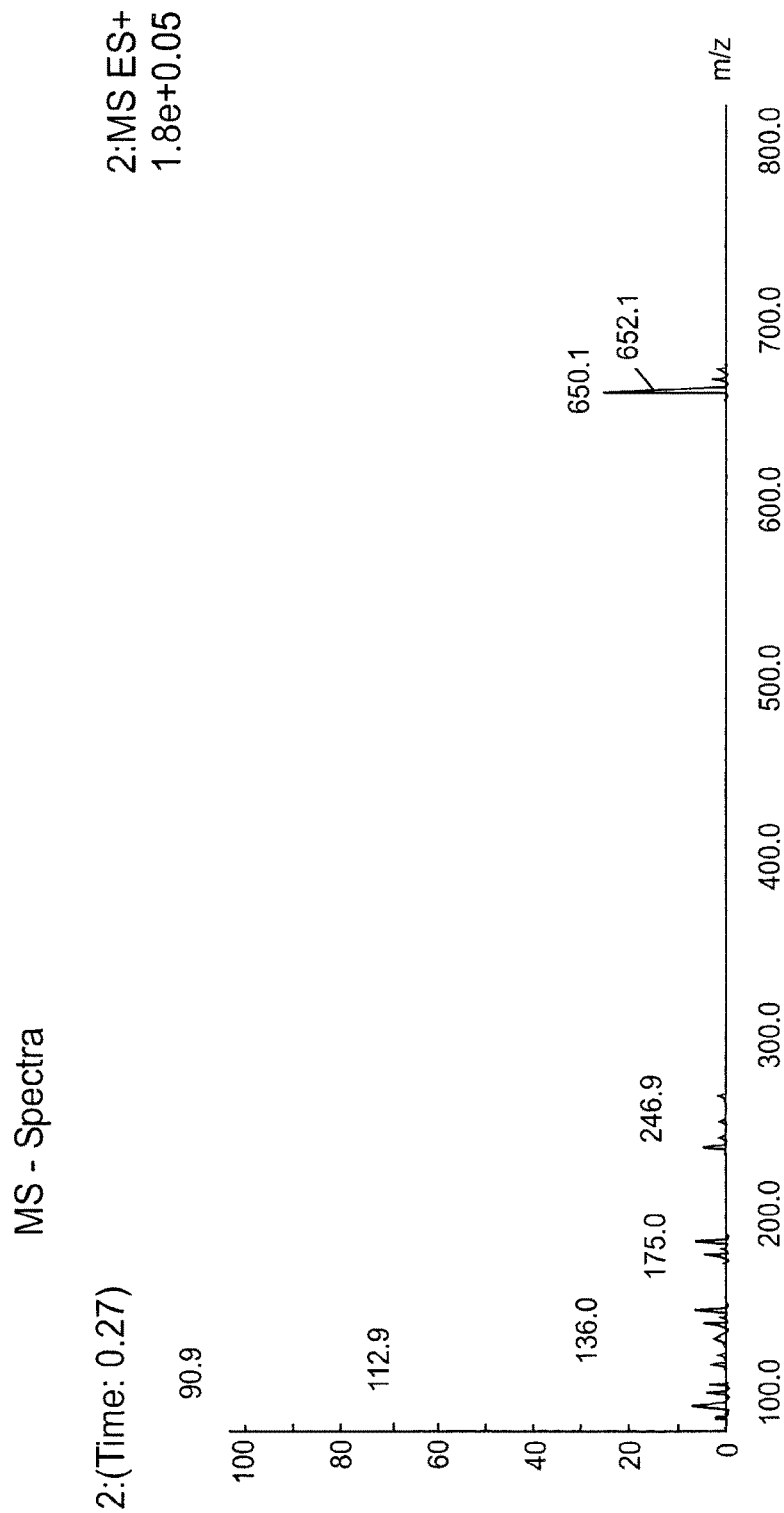
Figure 13:
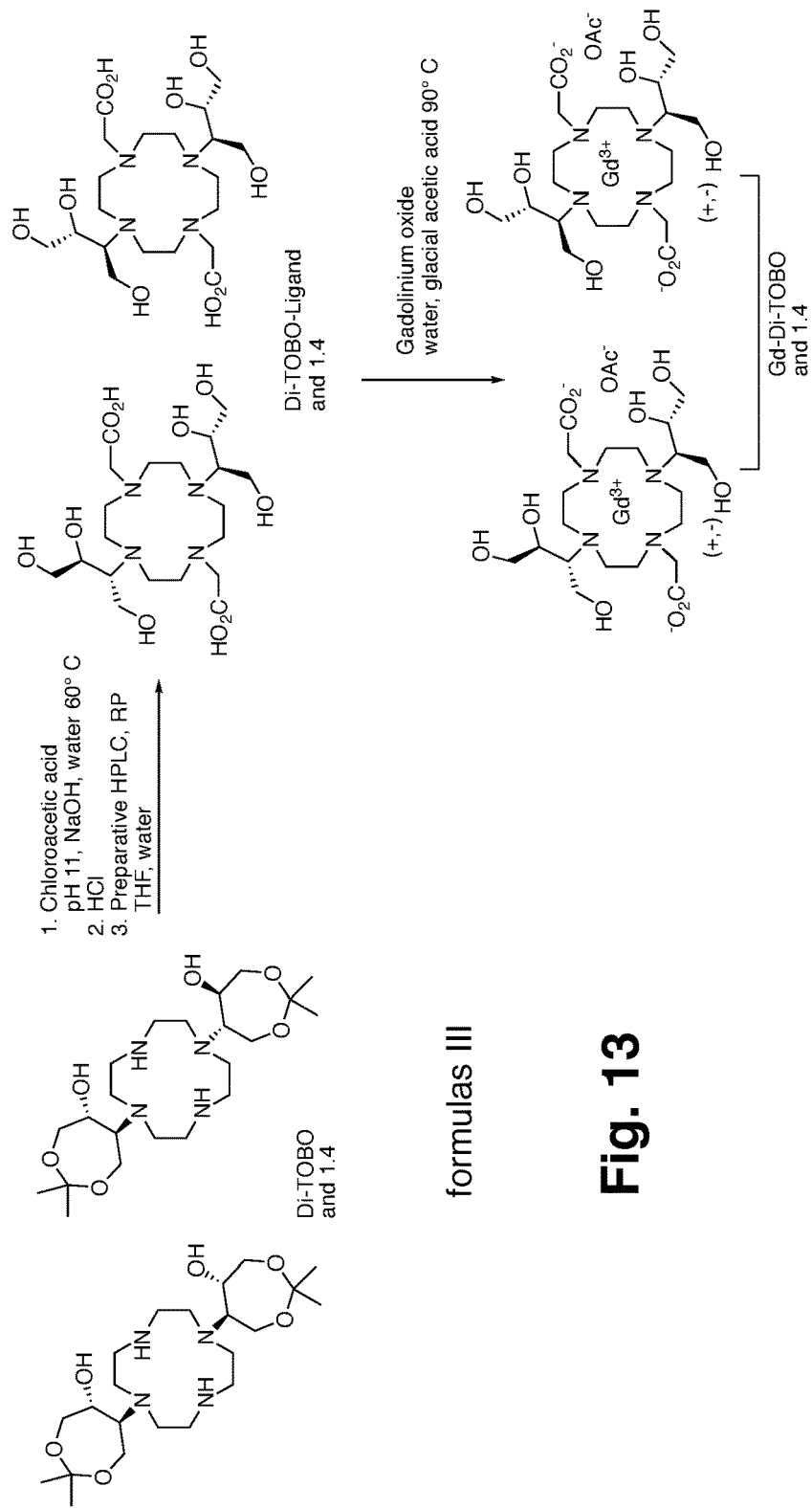
FIG. 13 illustrates formulas for a synthesis according to one aspect.

See FIG. 13, formulas III
See FIG. 5 MS-Spectra

Example 1

Preparation of Gadobutrol (Gd Complex of N-(1-hydroxymethyl-2,3-dihydroxypropyl)-1,4,7-triscarboxymethyl-1,4,7,10-tetraazacyclododecane)

Similarly to Example 1 and Example 5 of the laid-open publication EP 0986548 B1, starting with cyclen, gadobutrol, crude is prepared in a one-pot reaction and then purified on ion exchangers and finally converted by crystallization into gadobutrol, pure.

A. Preparation of Gadobutrol, Crude 160 kg of cyclen (1,4,7,10-tetraazacyclododecane), 154 kg of 4,4-dimethyl-3,5,8-trioxabicyclo[5,1,0]octane and 34.7 kg of lithium chloride are initially charged in 325 kg of isopropanol and heated under reflux for 1320 minutes.

1250 L of water are added, and the mixture is distilled until an internal temperature of 78° C. is reached. The mixture is then made up with 805 L of water, and 375 kg of sodium monochloroacetate are added at 35° C., followed by 120 kg of 50% strength aqueous sodium hydroxide solution. The mixture is heated to an internal temperature of 65° C., and a further 85 kg of 50% strength aqueous sodium hydroxide solution are added. If the pH drops below 12, it is re-adjusted with 10 kg of 50% strength aqueous sodium hydroxide solution (step-wise). The mixture is stirred at an internal temperature of 65° C. for 90 minutes. After cooling to 50° C., 240 kg of 36% aqueous hydrochloric acid are added such that the pH is now 3.1-4.9 (if appropriate, additional hydrochloric acid has to be added; it is important that the target pH is reached). At a jacket temperature of 95° C. and under reduced pressure, solvent (isopropanol/water mixture) is then distilled off to a total amount of 1200 kg.

At 40° C., 2554 kg of methanol are added and the pH is adjusted to 1.4 or less (1.1-1.3, optimum 1.2) using 282 kg of 36% aqueous hydrochloric acid. The mixture is stirred at 40° C. for 35 minutes. The mixture is then cooled to 20° C. and the precipitated sodium chloride (NaCl) is separated off using a centrifuge or a pressure nutsche filter (the filter cake is washed with methanol since the product is in solution). 996 L of water are added, and the methanol is substantially distilled off at a jacket temperature of 90° C. (250 mbar), with water, the mixture is concentrated to a mass of 966 kg, and a further 1200 L of water are then added. 155 kg of gadolinium oxide are added to this solution, and the mixture is heated at 95° C. for 120 minutes. The mixture is allowed to cool to 50° C. and adjusted to pH 7.1-7.4 using lithium hydroxide monohydrate (this requires about 85 kg of lithium hydroxide monohydrate). At a jacket temperature of 120° C. and under reduced pressure, 895 kg of water are then distilled off. The mixture is allowed to cool to 73° C., 5286 kg of alcohol (MEK=methyl ethyl ketone denaturized) are added and the water content is checked using the Karl-Fischer method. The water content is adjusted to 8.5%. (If the value is less than 7.0, an appropriately calculated amount of water is added. If the value is greater than 9.5%, an appropriate amount of ethanol is added. For the process, it is important that the value is in the range from 7.0 to 9.5).

The mixture is then heated under reflux (78° C.) for 60 minutes. Eventually, spontaneous crystallization occurs. The mixture is stirred at a jacket temperature of 100° C. for 480 minutes and then allowed to cool to 20° C.

The product is isolated using a centrifuge or pressure nutsche, the filter cake twice being washed with ethanol. In a paddle drier, the crude product is dried at a jacket temperature of 58° C. for 90 minutes under reduced pressure (until a pressure of <62 mbar and a temperature of >46° C. are reached) or washed with ethanol three times and dried at <34° C. The product is then dried at an internal temperature of 48° C. for 60 minutes. The crude product is cooled to 20° C. and filled into containers. This gives 540 kg of a colourless crystalline powder (yield>96%).

B. Ion Exchanger Purification of Gadobutrol, Crude

Part of the batch prepared above is purified as follows:

120 kg of gadobutrol, crude are dissolved in 1200 kg of water and initially pumped onto a column which contains acidic ion exchanger (AMBERLITE IRC 50). The eluate is pumped directly onto a column which basic ion exchanger (IRA 67) and the eluate is then pumped back onto the acidic ion exchanger (and so forth). The solution is recirculated until a conductivity limit value of <20 μS/cm is reached.

The solution is transferred to a thin-layer evaporator and carefully concentrated at 50 mbar (89 kg in about 585 L of water, yield 74.1%).

C. Final Crystallization to Gadobutrol, Crude 16 kg of activated carbon NORIT SX PLUS are added to 324 kg of gadobutrol, crude (19.1-20.9% strength solution in water) (conductivity 20 μS), and the mixture is stirred at 20° C. for 60 minutes. The activated carbon is filtered off and washed twice with water. The product-containing filtrate solution is then filtered through a sterile filter candle and concentrated at a jacket temperature of 80° C. under reduced pressure (amount of distillate about 1600 L). The jacket temperature is then raised to 75° C. and, in a first step, 100 kg of alcohol are metered in, the jacket temperature is then increased to 98° C. (>75° C. internal temperature), and a further 1360 kg of alcohol are added such that the internal temperature does not drop below 72° C. (total time for the metered addition about 120 minutes). At this point in time, the water content of the solution is determined according to Karl-Fischer. Ideally, the value should be 10-12%. If the value is higher or lower, it is adjusted to 11% exactly by addition of water or alcohol (in small portions). Once the desired water content is achieved, the mixture is heated under reflux for 120 minutes. The mixture is allowed to cool to 20° C., the product is isolated using a centrifuge or pressure nutsche and the filter cake is washed with ethanol. The product is then dried under reduced pressure (jacket temperature 55° C.) until an internal temperature of >53° C. is reached. The product is then filled into aluminium-coated PE bags.

Yield: 314 kg (96.9% of theory) of a colourless crystalline powder, polymorph I

Water content (Karl-Fischer): 3.1%

Amount of residual ethanol solvent: <200 ppm

Content: 100.4% (compared to external reference)

HPLC (100% method): >99.7% (99.8 or 99.9%)

Free $Gd^{3+}$: <0.01%

Butrol ligand: <0.03%

Di-TOBO ligand generally <0.03%

Gd-DO3A: not detectable <0.03%

Endotoxin: <0.5 EU

Unspecified impurities: <0.03%

The table below shows the analytical data of 6 batches taken during the course of the gadobutrol production and produced by the process described above:

|  | Specification | Batch No. 1 | 2 | 3 | 4 | 5 | 6 |
|---|---|---|---|---|---|---|---|
|  |  | Batch size [kg] | | | | | |
|  |  | 338.1 | 254.2 | 446.6 | 209.6 | 241.9 | 289.6 |
| Ethanol: (GC) | ≤2000 ppm | <LOQ | <LOQ | <LOQ | <LOQ | <LOQ | <LOQ |
| Impurities: (HPLC) | butrol ≤ 0.05% | <0.03%* | <0.03%* | <0.03%* | <0.03%* | <0.03%* | <0.03%* |
| Impurities: (HPLC) | any unspecified ≤ 0.05% | <0.03%* | <0.03%* | <0.03%* | <0.03%* | <0.03%* | <0.03%* |
| Impurities: (HPLC) | total ≤ 0.30% | <0.03% | <0.03% | <0.03% | <0.03% | <0.03% | <0.03% |
| Free gadolinium: (photometric titration) | ≤0.01% ** | <0.01% | <0.01% | <0.01% | <0.01% | <0.01% | <0.01% |
| Water: (Karl Fischer) | ≤7.0% | 3.1% | 3.1% | 3.1% | 3.4% | 3.2% | 3.1% |
| Gadolinium content: (ICP) | 255 to 265 mg/g | 260 mg/g | 259 mg/g | 255 mg/g | 259 mg/g | 263 mg/g | 261 mg/g |
|  | 98.0 to 102.0%, calculated as gadobutrol ** | 99.9% | 99.7% | 99.7% | 99.7% | 101.0% | 100.3% |
| Test for gadobutrol: (HPLC) | 98.0 to 102.0% ** | 100.2% | 100.4% | 100.2% | 100.3% | 100.9% | 100.0% |

Example 2

Characterization of Polymorphs I and II

1. X-ray diffraction

The graphical illustrations below show the X-ray diffraction spectra of the two polymorphs compared to the amorphous material.

Method

X-Ray Powder Diffraction (XRPD)

The measurement was carried out in transmission mode using the STOE Powder Diffractometer STADI P.

Detector: linear position sensitive detector

Radiation: germanium-monochromatized CuKα1-radiation (λ=1.5406 Å)

Mode: transmission

Scan range: 3°≤2Θ≤40° or 3°≤2Θ≤35°

Stepwidth: 0.5° or 1.0°

Measuring time: t≥60 s/step

Sample preparation: thin layer

Figure 6:
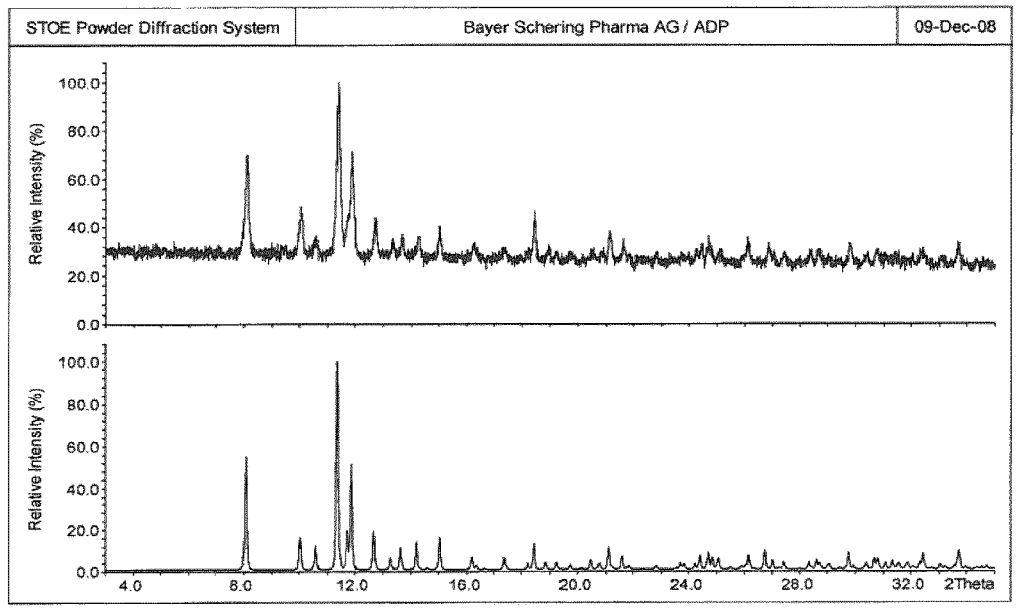
FIG. 6 illustrates the X-ray diffractogram of polymorph monohydrate of Gadobutrol (Top) compared to the calculated theoretical diffractogram of the Gadobutrol monohydrate (Bottom).

See FIG. 6 X-Ray diffractogram of polymorph I monohydrate I compared to the calculated theoretical diffractogram of the monohydrate.

Figure 7:
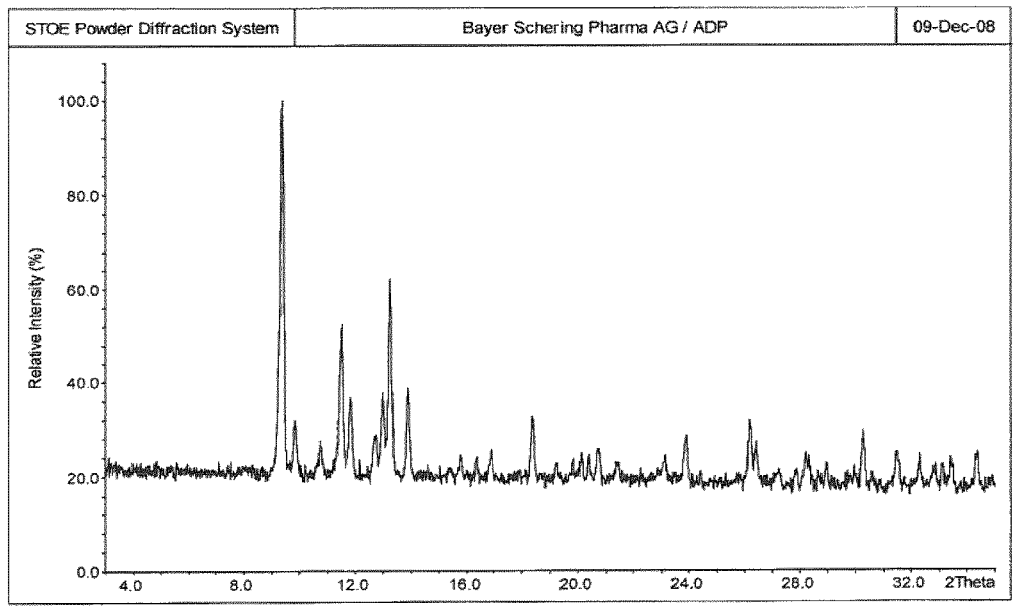
FIG. 7 illustrates an X-ray diffractogram of Gadobutrol polymorph II monohydrate II.

See FIG. 7, X-Ray diffractogram of polymorph II monohydrate II.

Figure 8:
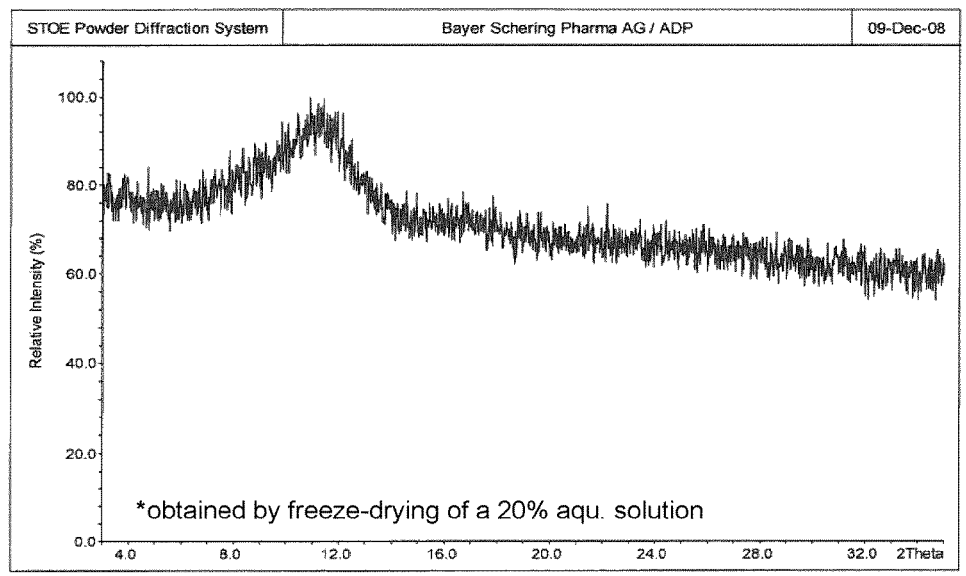
FIG. 8 illustrates an X-ray diffractogram of amorphous gadobutrol.

See FIG. 8, X-ray diffractogram of amorphous gadobutrol.

2. IR Spectra

Figure 9:
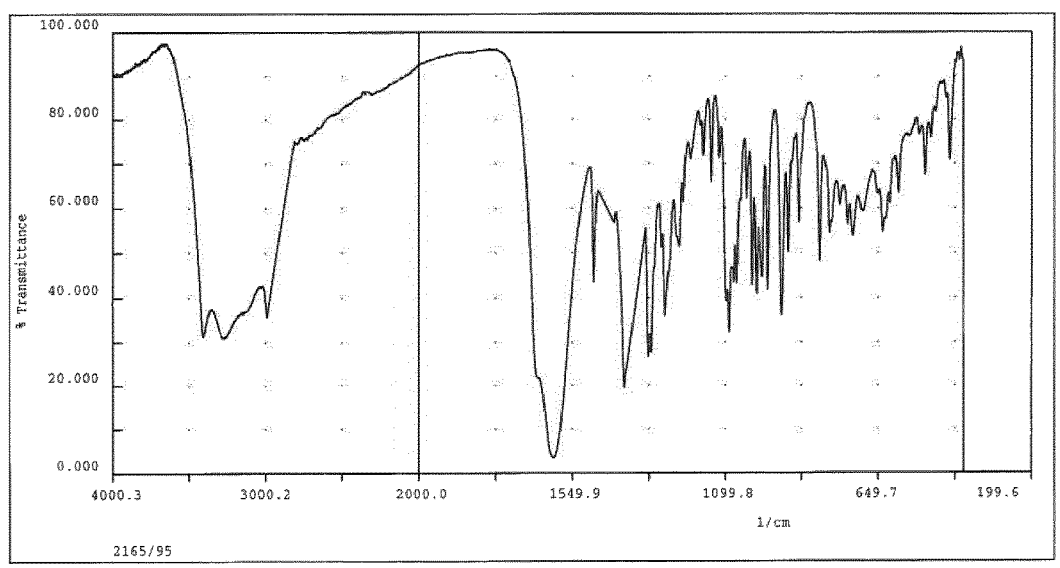
FIG. 9 illustrates an IR Spectrum of Gadobutrol monohydrate, (nujol preparation).

See FIG. 9, IR spectrum of monohydrate I (nujol preparation)

Figure 10:
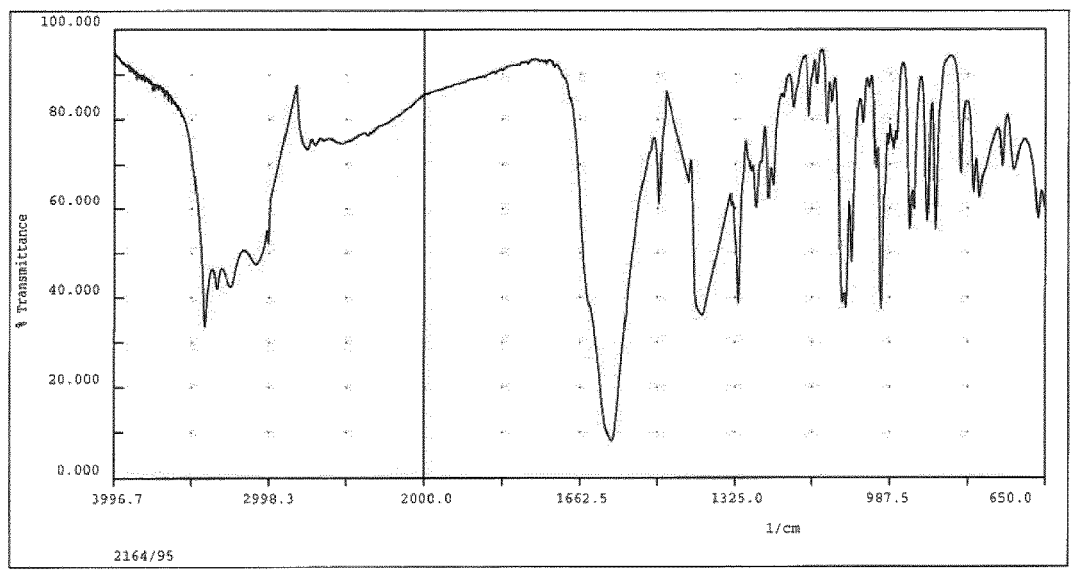
FIG. 10 illustrates an IR Spectrum of Gadobutrol monohydrate II, (nujol preparation).

See FIG. 10, IR spectrum of monohydrate II (nujol preparation)

Figure 11:
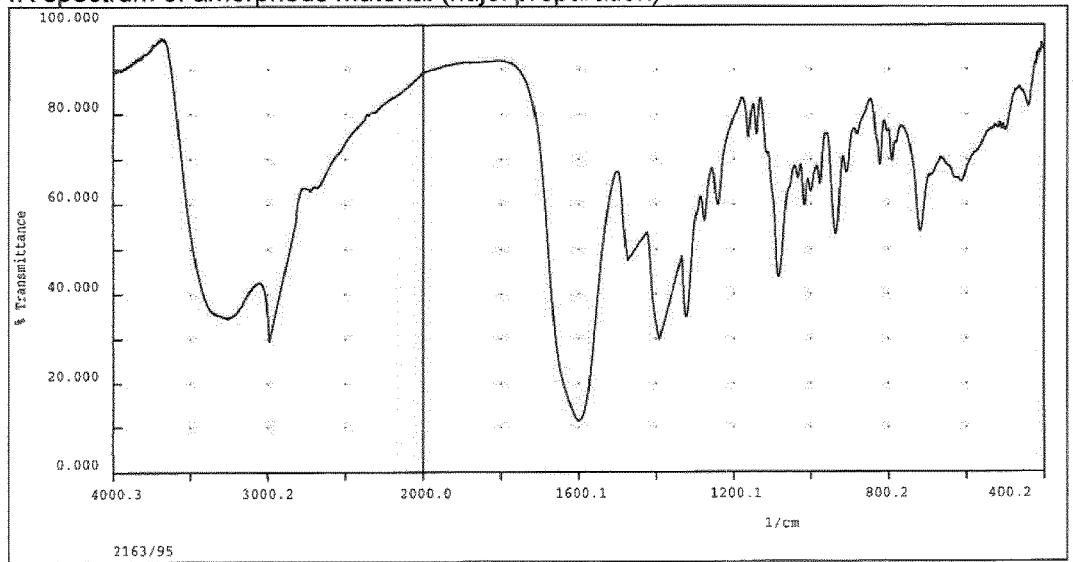
FIG. 11 illustrates an IR Spectrum of amorphous material (nujol preparation).

FIG. 11, IP spectrum of amorphous material (nujol preparation)

3. Differential Thermal Analysis (DTA) and Thermogravimetry (TG) Method

Simultaneous DTA/TG measurements are recorded on a Seteram DSC 111.

Heating rates: 5 K/min

Temperature range: 25° C.-250° C. (partly up to 500° C.)

Purge gas: dry nitrogen

Sample holder: aluminium crucibles

See FIG. 1, DTA/TG traces of monohydrate I

See FIG. 2, DTA/TG traces of monohydrate II

See FIG. 3, DTA/TG traces of the amorphous phase

What is claimed is:

1. A process for producing a high-purity gadobutrol (N-(1 hydroxymethyl-2,3-dihydroxypropyl)-1,4,7-triscarboxymethyl-1,4,7,10-tetraazacyclododecane), the process comprising:
    crystallizing a crude gadobutrol product from a first ethanol solution having a water content of 7.0 to 9.5%;
    isolating a crystallized crude gadobutrol;
    treating an aqueous solution of the crystallized crude gadobutrol on an ion exchange column cascade to produce a gadobutrol eluate until the gadobutrol eluate has a conductivity of less than 40 μS/cm;
    concentrating the gadobutrol eluate having the conductivity of less than 40 μS/cm to provide a concentrated gadobutrol eluate;
    crystallizing the concentrated gadobutrol eluate from a second ethanol solution having a water content of 10.0 to 12.0% to give a purified gadobutrol in crystalline form; and
    isolating and drying the purified gadobutrol to give the high-purity gadobutrol.

2. The process of claim 1, wherein crystallizing the crude gadobutrol product comprises: heating the first ethanol solution having the water content of 7.0 to 9.5% under reflux; and cooling the first ethanol solution having the water content of 7.0 to 9.5% to form the crystallized crude gadobutrol.

3. The process of claim 2, wherein the first ethanol solution has a water content of 8.0 to 9.0%.

4. The process of claim 1, wherein the ion exchange column cascade comprises an acidic ion exchange column followed by a basic ion exchange column.

5. The process of claim 1, wherein treating the aqueous solution of the crystallized crude gadobutrol comprises repeatedly treating the aqueous solution of crystallized crude gadobutrol on the ion exchange column cascade until the gadobutrol eluate has a conductivity of less than 20 μS/cm.

6. The process of claim 1, wherein crystallizing the concentrated gadobutrol eluate comprises: heating the second ethanol solution having the water content of 10.0 to 12.0% under reflux; and cooling the second ethanol solution having the water content of 10.0 to 12.0% to give the purified gadobutrol in crystalline form.

7. The process of claim 6, wherein crystallizing the concentrated gadobutrol eluate further comprises:
    treating the concentrated gadobutrol eluate with activated carbon; filtering to remove the activated carbon; and adding sufficient ethanol to adjust the water content of the second ethanol solution to 10.0 to 12.0% prior to heating the second ethanol solution.

8. The process of claim 6, wherein the second ethanol solution has a water content of 10.5 to 11.5%.

9. The process of claim 1, wherein the high-purity gadobutrol has a purity of greater than 99.7% as determined by high performance liquid chromatography (HPLC).

10. The process of claim 9, wherein the high-purity gadobutrol is a polymorph I monohydrate polymorph of gadobutrol.

11. The process of claim 9, wherein the high-purity gadobutrol has less than 0.01% free $Gd^{3+}$, less than 0.03% free butrol (N-(1-hydroxymethyl-2,3-dihydroxypropyl)-1,4,7-triscarboxymethyl-1,4,7,10-tetraazacyclododecane) ligand, and less than 0.06% of poly(1-hydroxymethyl-2,3-dihydroxypropyl) cyclen byproducts.

12. The process of claim 1, wherein the high-purity gadobutrol has a purity of greater than 99.8% as determined by high performance liquid chromatography (HPLC).

13. The process of claim 1, further comprising synthesizing the crude gadobutrol product by a process comprising:
reacting cyclen (1,4,7,10-tetraazacyclododecane) with 4,4-dimethyl-3,5,8-trioxabycicly[5.1.0]octane and lithium chloride to produce an N-(6-hydroxy-2,2-dimethyl-1,3-dioxepan-5-yl)-(1,4,7,10-tetraazacyclododecane)/LiCl complex;
alkylating the N-(6-hydroxy-2,2-dimethyl-1,3-dioxepan-5-yl)-(1,4,7,10-tetraazacyclododecane)/LiCl complex with sodium monochloroacetate to produce a medium containing an alkylated intermediate;
acidifying the medium containing the alkylated intermediate to produce an acidified medium;
precipitating and removing any salts from the acidified medium containing the alkylated intermediate to provide a medium containing butrol (N-(1-hydroxymethyl-2,3-dihydroxypropyl)-1,4,7-triscarboxymethyl-1,4,7,10-tetraazacyclododecane);
adding gadolinium oxide to the medium containing the butrol to complex a gadolinium ion ($Gd^{3+}$) with the butrol to form a solution of the crude gadobutrol product;
neutralizing the pH of the solution of the crude gadobutrol product to a pH of from 7.1-7.4 to form a neutralized solution of the crude gadobutrol product;
concentrating the neutralized solution of the crude gadobutrol product; and
adding sufficient ethanol to provide the crude gadobutrol product in the ethanol solution having the water content of 7.0 to 9.5%.

14. The process of claim 1, wherein the process is conducted on an industrial scale.

15. The process of claim 1, further comprising adding from 0.08 to 0.14% of calcobutrol.

16. A process for producing a high-purity gadobutrol (N-(1-hydroxymethyl-2,3-dihydroxypropyl)-1,4,7-triscarboxymethyl-1,4,7,10-tetraazacyclododecane), the process comprising:
crystallizing a crude gadobutrol product from a first ethanol solution having a water content of 7.0 to 9.5%;
isolating a crystallized crude gadobutrol;
repeatedly treating an aqueous solution of the crystallized crude gadobutrol on an ion exchange column cascade comprising an acidic ion exchange column followed by a basic ion exchange column to produce a gadobutrol eluate until the gadobutrol eluate has a conductivity of less than 40 μS/cm;
concentrating the gadobutrol eluate having the conductivity of less than 40 μS/cm to provide a concentrated gadobutrol eluate;
crystallizing the concentrated gadobutrol eluate from a second ethanol solution having a water content of 10.0 to 12.0% to give a purified gadobutrol in crystalline form; and
isolating and drying the purified gadobutrol to give the high-purity gadobutrol having a purity of greater than 99.7% as determined by high performance liquid chromatography.

17. The process of claim 16, further comprising synthesizing the crude gadobutrol product by a process comprising:
reacting cyclen (1,4,7,10-tetraazacyclododecane) with 4,4-dimethyl-3,5,8-trioxabycicly[5.1.0]octane and lithium chloride to produce an N-(6-hydroxy-2,2-dimethyl-1,3-dioxepan-5-yl)-(1,4,7,10-tetraazacyclododecane)/LiCl complex;
alkylating the N-(6-hydroxy-2,2-dimethyl-1,3-dioxepan-5-yl)-(1,4,7,10-tetraazacyclododecane)/LiCl complex with sodium monochloroacetate to produce a medium containing an alkylated intermediate;
acidifying the medium containing the alkylated intermediate to produce an acidified medium;
precipitating and removing any salts from the acidified medium containing the alkylated intermediate to provide a medium containing butrol (N-(1-hydroxymethyl-2,3-dihydroxypropyl)-1,4,7-triscarboxymethyl-1,4,7,10-tetraazacyclododecane);
adding gadolinium oxide to the medium containing the butrol to complex a gadolinium ion ($Gd^{3+}$) with the butrol to form a solution of the crude gadobutrol product;
neutralizing the pH of the solution of the crude gadobutrol product to a pH of from 7.1-7.4 to form a neutralized solution of the crude gadobutrol product;
concentrating the neutralized solution of the crude gadobutrol product; and
adding sufficient ethanol to provide the crude gadobutrol product in the ethanol solution having the water content of 7.0 to 9.5%.

18. The process of claim 16, wherein the high-purity gadobutrol is a polymorph I monohydrate polymorph of gadobutrol.

19. The process of claim 16, wherein the high-purity gadobutrol has less than 0.01% free $Gd^{3+}$ ions and less than 0.03% of free butrol ligand.

20. The process of claim 16, further comprising adding from 0.08 to 0.14% of calcobutrol.

* * * * *